(12) United States Patent
Amer

(10) Patent No.: US 8,324,247 B2
(45) Date of Patent: Dec. 4, 2012

(54) METHOD FOR TREATING PULMONARY ARTERIAL HYPERTENSION

(75) Inventor: Moh. Samir Amer, Montecito, CA (US)

(73) Assignee: Ventrus Biosciences, Inc., New York, NY (US)

( * ) Notice: Subject to any disclaimer, the term of this patent is extended or adjusted under 35 U.S.C. 154(b) by 484 days.

(21) Appl. No.: 12/577,795

(22) Filed: Oct. 13, 2009

(65) Prior Publication Data

US 2010/0099707 A1    Apr. 22, 2010

(51) Int. Cl.
*A61K 31/445* (2006.01)
*A61P 11/00* (2006.01)
(52) U.S. Cl. .................. 514/315; 514/319; 514/337
(58) Field of Classification Search .................. 514/315, 514/319, 337
See application file for complete search history.

(56) References Cited

U.S. PATENT DOCUMENTS 5,780,487 A    7/1998    Amer

FOREIGN PATENT DOCUMENTS

| WO | 2005/063220 A1 | 7/2005 |
| WO | 2008/061966 A2 | 5/2008 |

OTHER PUBLICATIONS

Launay, J. M., "Function of the serotonin 5-hydroxytryptamine 2β receptor in pulmonary hypertension", Nature Medicine, vol. 8, No. 10, Oct. 2002, pp. 1129-1135.

Dempsie, Y., et al., "Role of the serotonin transporter in pulmonary arterial hypertension", Expert Review of Clinical Pharmacology, 1(6), Jan. 1, 2008, pp. 749-757.

*Primary Examiner* — Sreeni Padmanabhan
*Assistant Examiner* — Sahar Javanmard
(74) *Attorney, Agent, or Firm* — Marianne Fuierer; Moore & Van Allen, PLLC

(57) ABSTRACT

Pulmonary arterial hypertension in a mammal can be prevented or treated using combined 5-HT2A and 5-HT2B receptor antagonist. The antagonists can be present in a single compound or in two separate compounds.

6 Claims, 2 Drawing Sheets

Effects of Iferanserin (p.o.) on Acute Hypoxia-Induced Pulmonary Hypertesion

Effects of Iferanserin (p.o.) on Acute Hypoxia-Induced Systemic Hypotension

METHOD FOR TREATING PULMONARY ARTERIAL HYPERTENSION

This application claims the benefit of U.S. Provisional Patent Application No.: 61/107,382 filed Oct. 22, 2008, which is hereby incorporated in its entirety.

FIELD OF THE INVENTION

This invention relates to the use of combined 5-HT$_{2A}$ and 5-HT$_{2B}$ receptor blockade whether using at least two separate compounds each capable of blocking one receptor or one compound capable of blocking both receptors for treating or preventing pulmonary arterial hypertension (PAH) in animals including mammals, especially humans.

BACKGROUND OF THE INVENTION

Although the pulmonary artery is an artery by definition since it carries blood away from the heart, it is a vein both structurally and functionally. Its wall thickness is similar to that of veins and it carries de-oxygenated blood at low pressure of less than 20 mmHg, which is significantly lower than the blood pressure in the arteries.

In pulmonary hypertension, the blood pressure in the pulmonary artery generally exceeds 25 mmHg at rest and 30 mmHg with exercise. This is mostly due to vasoconstriction of the pulmonary artery. Sustained elevated pulmonary vascular constriction and resistance to blood flow leads to the thickening of the pulmonary arterial walls, which sustains the elevated pressure. This condition is known as pulmonary arterial hypertension or PAH. In PAH, the pulmonary arteries show medial hypertrophy, intimal fibrosis, and plexiform lesions. Pumping the blood against increased resistance leads to right heart failure and death within two to three years.

Two common types of pulmonary artery hypertension exist: primary or idiopathic that is associated with thickened pulmonary arteries with very high pulmonary pressures (≈80/50) and secondary or hypoxic that is characterized by moderate pulmonary pressures (≈50/30).

Serotonin (5-Hydroxytryptamine, 5-HT) appears be involved in the etiology of elevated pulmonary arterial pressure (PAH), including its initiation and partial maintenance. Support for this includes the following:

1. Mice over-expressing the 5-hydroxytryptamine-transporter gene develop spontaneous and progressive pulmonary hypertension.
2. 5-HT causes contraction of the pulmonary artery.
3. Trophic action of 5-HT$_{2A}$ receptors in cardiomyocytes and the beneficial effects of ketanserin (a 5-HT$_{2A}$ serotonin blocker) in cardiac hypertrophy. Cardiac hypertrophy induced even by isoproterenol (a β-adrenergic receptor agonist) requires stimulation of 5-HT$_{2A}$ receptors.
4. Effects of dexfenfluramine in causing pulmonary hypertension are mediated by 5-HT$_{2B}$ receptors.
5. Hypoxia-induced rise in plasma serotonin possibly mediates the hypoxia induced pulmonary hypertension via stimulation of 5-HT$_{2B}$ receptors.
6. Total pulmonary resistance is correlated with plasma serotonin levels in pulmonary hypertensive animals and patients.
7. Hypoxia-induced vascular proliferation required the 5-HT$_{2A}$ receptor activity.
8. Nitric oxide (NO) is lacking in the pulmonary arteries of PAH patients. NO appears to be the final common mediator of vaso-relaxation. Serotonin reduces the levels of nitric oxide in vascular smooth muscle cells.
9. Pulmonary hypoxia results in red blood cell sickling, increased vascular adhesions and the release of serotonin from blood platelets which often lead to PAH.

The vasoconstrictor effects of serotonin, triggered through the 5-HT$_{2B}$ receptors, appear to be the initial triggers of the disease, which can be prevented by 5-HT$_{2B}$ antagonists. 5-HT levels are increased 10-30 times normal in patients with PAH and the 5-HT$_{2B}$ receptor population is increased ~3.5× in the pulmonary artery of patients with PAH.

Chronic PAH is partially maintained by physical and fixed alterations in the structure of walls of the small pulmonary arteries and arterioles. These changes which are induced to withstand the increased pressure and include vascular endothelial and smooth muscle cell proliferation, medial, predominantly smooth muscle cell, thickening, neo-intimal formation, and the subsequent obliteration of the vascular lumen. These effects appear to be mediated by 5-HT$_{2A}$ receptors.

Thus, serotonin appears to be involved in both the initiation, through vasoconstriction (5-HT$_{2B}$ receptors), and maintenance, through arterial wall thickening (5-HT-$_{2A}$ receptors) of PAH.

To ensure both prevention and treatment of PAH, both 5-HT$_{2A}$ and 5-HT$_{2B}$ receptors need to be blocked.

SUMMARY OF THE INVENTION

In accordance with certain of its aspects, the invention relates to the prevention and/or treatment of pulmonary arterial hypertension by combined 5-HT$_{2A}$ and 5-HT$_{2B}$ receptor blockade achieved by administering a therapeutically effective amount of a compound that is both a 5-HT$_{2A}$ and 5-HT$_{2B}$ receptor antagonist or a combination of two compounds to achieve the same objective.

Another aspect of the invention relates to the prevention and/or treatment of pulmonary arterial hypertension by administering a therapeutically effective amount of S-2'-[2-(1-methyl-2-piperidyl)ethyl] cinnamanilide (S-MPEC) (iferanserin) or a pharmaceutically acceptable acid salt thereof.

DETAILED DESCRIPTION OF THE INVENTION

Figure 1:
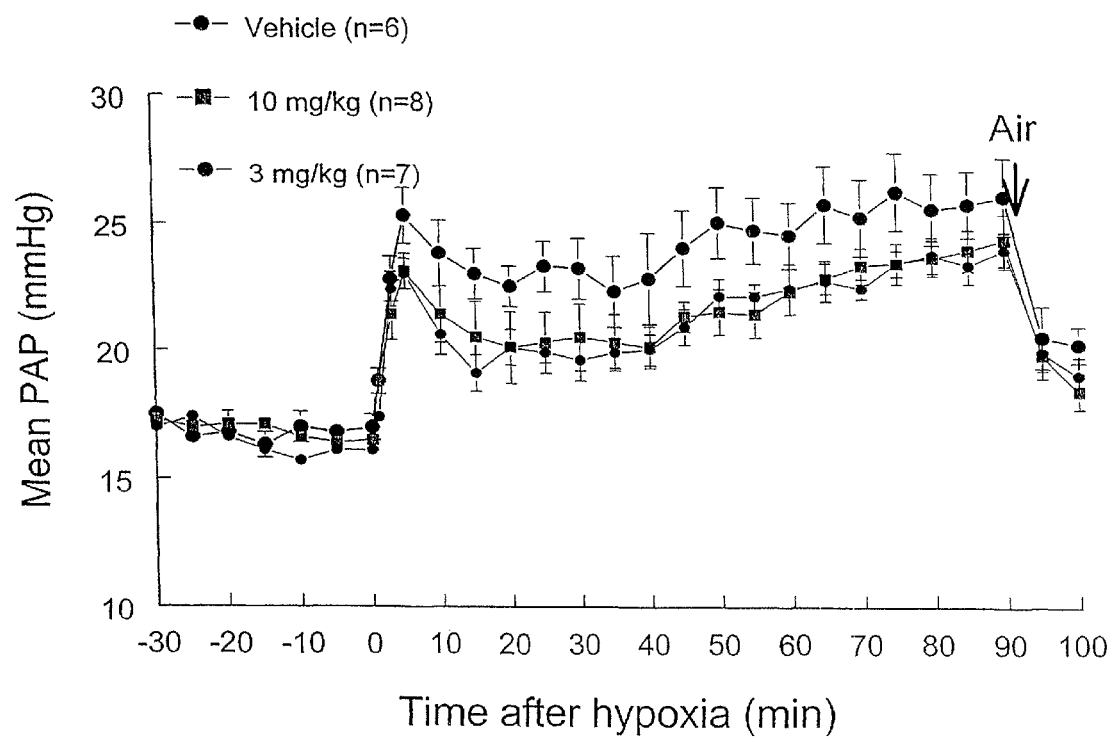
FIG. 1 is a graph illustrating the effects of iferanserin given orally on acute hypoxia-induced pulmonary hypertension.
Figure 2:
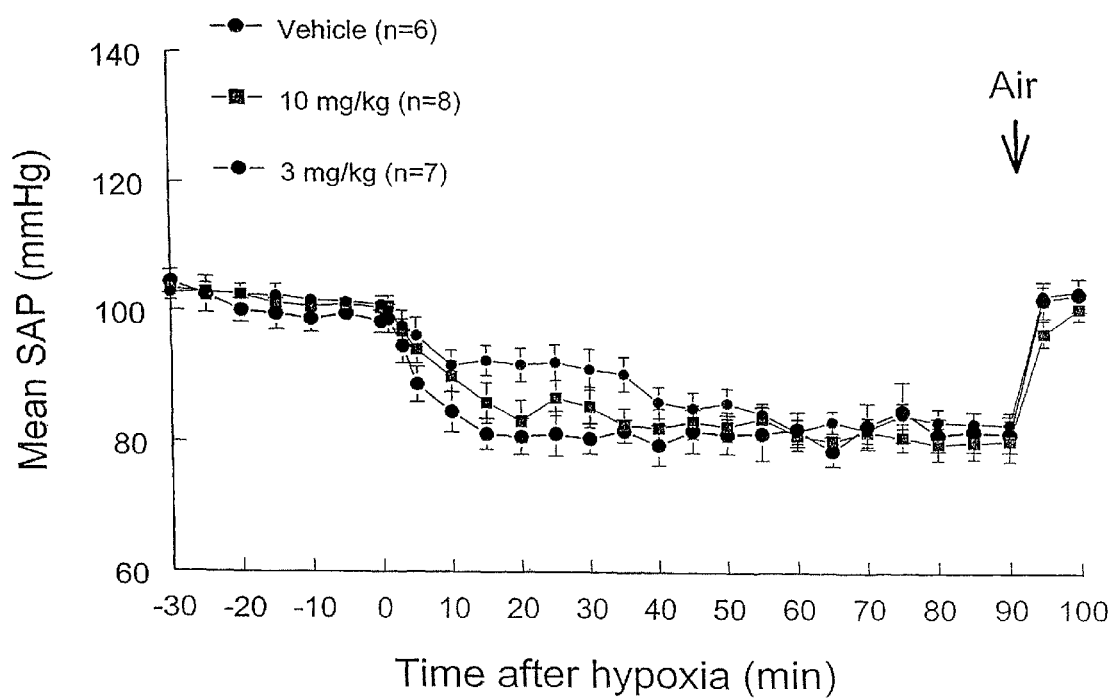
FIG. 2 is a graph illustrating the effects of iferanserin given orally on acute hypoxia-induced systemic hypotension.

Generally speaking, this invention is directed to a method of preventing and/or treating PAH in an animal or human body.

In particular the invention relates to the prevention and/or treatment of pulmonary arterial hypertension by administering a therapeutically effective amount of a compound that is both a 5-HT$_{2A}$ and 5-HT$_{2B}$ receptor antagonist to an animal including mammals in general and humans in particular, for the treatment or prevention and/or treatment of pulmonary arterial hypertension (PAH).

Another aspect of the invention relates to administering at least two separate compounds one that is a 5-HT$_{2A}$ receptor antagonist and a second that is a 5-HT$_{2B}$ receptor antagonist for treating and/or preventing pulmonary arterial hypertension (PAH) in animals including mammals, especially humans.

Iferanserin, S-2'-[2-(1-methyl-2-piperidyl) ethyl] cinnamanilide (S-MPEC), disclosed in U.S. Pat. No. 5,780,487, is both a 5-HT$_{2A}$ and 5-HT$_{2B}$ receptor antagonist and can be administered to an animal, including mammals in general and humans in particular, for prevention and/or treatment of pulmonary arterial hypertension (PAH).

The method comprises administering to such an animal or mammal, especially humans, who has or is at risk of developing PAH, an effective amount of a 5-HT$_{2A}$ and 5-HT$_{2B}$ receptor antagonist such as S-2'-[2-(1-methyl-2-piperidyl) ethyl] cinnamanilide (S-MPEC) or a pharmaceutically acceptable acid salt thereof.

S-2'-[2-(1-methyl-2-piperidyl) ethyl] cinnamanilide or its acid salt uniquely blocks both 5-HT$_{2A}$ and 5-HT$_{2B}$ receptors at a reasonable dose range. It is relatively safe, and with minimal activities on other receptors, consequently has minimal side effects. It is bio-available orally and has an acceptable half-life.

As described below, the effects of S-2'-[2-(1-methyl-2-piperidyl) ethyl] cinnamanilide in Acute Hypoxia-Induced Pulmonary Hypertension was measured and it was determined that iferanserin partially inhibited the acute hypoxia-induced pulmonary hypertension in adult rats. These results support the conclusion that S-2'-[2-(1-methyl-2-piperidyl) ethyl] cinnamanilide or a pharmaceutically acceptable salt thereof can be used for the treatment and/or prevention of PAH.

The combined 5-HT$_{2A}$ and 5-HT$_{2B}$ receptor antagonist(s) may be employed in free form or as a generally water soluble non-toxic pharmaceutically acceptable addition salt such as an basic or acidic addition salt such as for the acidic addition salt with such relatively non-toxic organic or inorganic acids as sulfuric, sulfonic, phosphoric, phosphonic, hydrobromic, hydrochloric, hydroiodic, sulfamic, methanesulfonic, benzenesulfonic, para-toluenesulfonic, acetic, lactic, succinic, malic, mucic, tartaric, citric, gluconic, benzoic, cinnamic, isethionic and the like.

The individual 5-HT$_{2A}$ and 5-HT$_{2B}$ receptor antagonists may also be employed in free form or as a generally water soluble non-toxic pharmaceutically acceptable acid or basic addition salt as described above.

Pharmaceutical compositions for use in the treatment or prevention of PAH may in the forms normally employed and may be taken orally; parenterally, by intravenous, subcutaneous, or intramuscular injection; or by inhalation therapy; or transdermally.

When multiple 5-HT receptor antagonists are used, they may be administered together, serially or in other ways such that the desired result is achieved. They may be administered by the same or different means and/or in the same or different suitable dosage forms.

For example, the composition containing a combined 5-HT$_{2A}$ and 5-HT$_{2B}$ receptor antagonist(s) or a pharmaceutically acceptable acid salt thereof, may be prepared and used in any suitable solid or liquid form, e.g. powder, paste, tablet, capsule, lozenge, gel, chewing gum, solution, suspension, emulsion, aerosol, syrup, elixir, aqueous or oily suspension, emulsion or solution or aerosol.

Suitably the compositions of this invention comprise sufficient active material(s) to provide a dose of from 0.05-100 mg. per kg. of body weight, more suitably 0.2-60 mg/kg body weight. These compositions may be taken 1-3 times daily or as needed until the symptom or condition being treated subsides or is corrected.

Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic or resulting in unacceptable side effects to the patient.

These compositions may contain the active ingredient in amounts ranging from less than 1% to over 99%, with the remainder being a pharmaceutically acceptable solid or liquid carrier, which may contain other conventional excipients. By "pharmaceutically acceptable" it is meant the carrier, diluent, excipient, and/or salt must be compatible with the other ingredients of the formulation, and not deleterious to the recipient thereof. Examples of such carriers and excipients include fillers, binders, flavors, sweeteners, bulking and coloring agents, antioxidants, anionic, nonionic, cationic, zwitterionic, and amphoteric surface active detergents, sudsing, dispersing and emulsifying agents, buffering and pH adjusting agents, water and organic solvents, humectants, thickeners, preservatives, stabilizers, mold release agents, disintegrants, anti-disintegrants, lubricants and the like. Examples of conventional pharmaceutically acceptable carriers and excipients are profusely disclosed in the prior art including discussions in U.S. Pat. No. 4,515,772 (Parran et al, Proctor & Gamble), U.S. Pat. No. 4,966,777 (Gaffar et al, Colgate-Palmolive Company), and U.S. Pat. No. 4,728,512 (Mehta et al, American Home Products), which discussions are incorporated herein by reference thereto.

The following example is only illustrative of certain preferred embodiments of this invention. All parts and proportions referred to herein and in the appended claims are by weight and temperatures are in degrees Centigrade, unless otherwise indicated.

EXAMPLE

Effects of MPEC in Acute Hypoxia-Induced Pulmonary Hypertension in Rats

METHODS

Measurement of Pulmonary and Systemic Arterial Pressure

Male Sprague-Dawley rats were obtained from Charles River Breeding Laboratories (Wilmington, Mass.) at 9-10 wk of age. For pulmonary arterial pressure measurement, a closed-chest technique (1-4). Under ketamine (80 mg/kg) and xylazine (5 mg/kg) anesthesia, a small transverse cut was made in the proximal right external jugular vein through passed. The introducer was a blunted 7.5 cm, 19-gauge needle with the tip turned up 30 degrees. The Silastic catheter filled with heparinsaline solution was passed through the introducer and attached by a 25 gauge blunted needle to a pressure transducer (model CP-01, Century Technology, Inglewood, Calif.) coupled to a polygraph (model 7, Grass Instruments, Quincy, Mass.). After the introducer was placed in the right ventricular cavity, the tip was directed anteriorly. The catheter was then advanced into the pulmonary artery. Catheter position was identified by the pressure tracing. The introducer was slipped out over the catheter and removed after a typical pulmonary arterial pressure tracing was recorded. The catheter was affixed to the vein and to the surrounding tissue distally by basketweave sutures and connected to polyethylene tubing (PE-10 fused to PE-20) with a loop. The PE-20 tubing was exteriorized at the back of the neck by a stainless steel wire (0.018 in. diam.) tunneled subcutaneously. For systemic arterial pressure measurement, an arterial cannula (PE-10 fused to PE-50) was inserted into the femoral artery, advanced into the dorsal aorta, and the PE-50 tubing was also exteriorized at the back of the neck. One day after catheterization, mean pulmonary arterial pressure (MPAP), mean systemic arterial pressure (MSAP) were recorded through the pulmonary and femora arterial catheters via transducers coupled to the polygraph.

On the day of the testing of rat's response to acute hypoxic exposure, after stable MSAP and MPAP recordings were obtained from the conscious unrestrained rats, iferanserin (3 and 10 mg/kg, dissolved in 0.9% saline at pH 5.5, or 3% Gum Arabic) or vehicle was administered orally 45 min before exposure to normobaric hypoxia (10% $O_2$, 1 atm). Rats were maintained in hypoxia for 90 min and then returned to normoxia (room air) for 15 min before the termination of MPAP and MSAP measurement.

Hypoxic Chamber and Exposure

Rats were exposed to hypoxia in a 330-liter Plexiglas glove box (Manostat, Brookyln, N.Y.) (1-4). Hypoxic exposures (range 10.0 +0.5% $O_2$) were accomplished by intermittently adding $N_2$ (Southern Welding, Birmingham, Ala.) to the chamber from a liquid $N_2$ reservoir, the gas outflow of which was regulated by a solenoid valve controlled by the recorder output of an S3-A O2 analyzer (Applied Electrochemistry, Sunnyvale, Calif.) through a control circuit (model 371-K, LFE, Clinton, Mass.). A baralyme $CO_2$ scrubber (Allied Health Care Products, St. Louis, Mo.) kept the $CO_2$ concentration at <0.2%. Relative humidity within the chamber was kept at <70% with anhydrous $CaSO_4$. Boric acid was used to keep $NH_3$ levels within the chamber at a minimum. Animals were permitted to have standard laboratory chow and tap water ad libitum.

Iferanserin partially inhibited the acute hypoxia-induced pulmonary hypertension in adult rats. There were no dose-dependent response within the range of 3-10 mg/kg, p.o.

This invention has been disclosed with respect to certain preferred embodiments, and it will be understood that modifications and variations thereof obvious to those skilled in the art are to be included within the spirit and purview of this application and the scope of the appended claims.

REFERENCES

1. Oparil S, Chen S J, Meng Q C, Elton T S, Yano M, Chen Y F. Endothelin-A receptor antagonist prevents acute hypoxia induced pulmonary hypertension in the rat. Am J Physiol 1995;268: L95-L100.
2. Li H, Oparil S., Meng O C, Elton T S, Chen Y F, Selective down-regulation of ANP clearance receptor gene expression in lung of rats adapted to hypoxia. Am J Physiol 199;268: L328-L335.
3. Chen S J, Chen Y F, Meng Q C, Durand J. DiCarlo V S, Oparil S. Endothelin receptor antagonist bosentan prevents and reverses hypoxia induced pulmonary hypertension in rats. J Appl Physiol 1995;79:2122-2131.
4. Tilton R G, Munsch C L, Sherwood S J, Chen Y F, WuC, Brock N. Dixon R A, Brock T A. Attenuation of pulmonary vascular hypertension and cardiac hypertrophy with sitaxsentan, an orally ET(A) receptor antagonist. Pul Pharmacol Ther 2000;13:87-97.

The invention claimed is:

1. A method for treating pulmonary arterial hypertension (PAH) by blocking both $5\text{-}HT_{2A}$ and $5\text{-}HT_{2B}$ receptors in a pulmonary artery comprising administering to a patient in need thereof a combined $5\text{-}HT_{2A}$ and $5\text{-}HT_{2B}$ receptor antagonist at a therapeutically effective dose, wherein the antagonist is S-2'-[2-(1-methyl-2-piperidypethyl] cinnamanilide (S -MPEC) or a pharmaceutically acceptable salt thereof.

2. The method according to claim 1, wherein the combined $5\text{-}HT_{2A}$ and $5\text{-}HT_{2B}$ receptor antagonist is administered orally, parenterally, intravenously, subcutaneously, intramuscularly, transdermally or by inhalation.

3. The method according to claim 1, wherein the dose is from 0.05-100 mg per kg of body weight.

4. A method for treating pulmonary arterial hypertension (PAH) comprising administering to a patient in need thereof a combined $5\text{-}HT_{2A}$ and $5\text{-}HT_{2B}$ receptor antagonist at a therapeutically effective dose, wherein the antagonist is S-2' [2-(1-methyl-2-piperidypethyl] cinnamanilide (S-MPEC) or a pharmaceutically acceptable salt thereof.

5. The method according to claim4, wherein the combined $5\text{-}HT_{2A}$ and $5\text{-}HT_{2B}$ receptor antagonist is administered orally, parenterally, intravenously, subcutaneously, intramuscularly, transdermally or by inhalation.

6. The method according to claim 4, wherein the dose is from 0.05-100 mg per kg of body weight.

* * * * *